(12) United States Patent
Gin et al.

(10) Patent No.: US 8,236,348 B2
(45) Date of Patent: Aug. 7, 2012

(54) LONG-LASTING, FLAVORED DOSAGE FORMS FOR SUSTAINED RELEASE OF BENEFICIAL AGENTS WITHIN THE MOUTH

(75) Inventors: Jerry B. Gin, Sunnyvale, CA (US); Benjamin F. Ross, Santa Clara, CA (US)

(73) Assignee: Bennes, Inc., Sunnyvale, CA (US)

( * ) Notice: Subject to any disclaimer, the term of this patent is extended or adjusted under 35 U.S.C. 154(b) by 1286 days.

(21) Appl. No.: 10/772,781

(22) Filed: Feb. 4, 2004

(65) Prior Publication Data

US 2004/0247669 A1    Dec. 9, 2004

Related U.S. Application Data

(63) Continuation-in-part of application No. 10/358,602, filed on Feb. 4, 2003, now abandoned.

(51) Int. Cl.
| | |
|---|---|
| A61K 9/20 | (2006.01) |
| A61K 9/00 | (2006.01) |
| A61K 8/00 | (2006.01) |
| A61K 36/534 | (2006.01) |

(52) U.S. Cl. ......... 424/464; 424/49; 424/400; 424/480; 424/725; 424/747; 433/215; 514/959

(58) Field of Classification Search ................. 424/49, 424/400, 464, 480
See application file for complete search history.

(56) References Cited

U.S. PATENT DOCUMENTS

| | | | |
|---|---|---|---|
| 1,526,039 A | 2/1925 | Arkell et al. | |
| 3,818,107 A | 6/1974 | Yolles | |
| 3,857,964 A | 12/1974 | Yolles | |
| 3,870,790 A | 3/1975 | Lowey et al. | |
| 3,920,849 A | 11/1975 | Marmo et al. | |
| 4,001,438 A | 1/1977 | Marmo et al. | |
| 4,039,653 A | 8/1977 | DeFoney et al. | |
| 4,259,355 A | 3/1981 | Marmo et al. | |
| 4,386,106 A | 5/1983 | Merritt et al. | |
| 4,391,824 A | 7/1983 | Siuta et al. | |
| 4,503,070 A | 3/1985 | Eby, III et al. | |
| 4,528,125 A * | 7/1985 | Alderman et al. | ................. 512/4 |
| 4,568,560 A | 2/1986 | Schobel | |
| 4,572,832 A * | 2/1986 | Kigasawa et al. | .......... 514/772.1 |
| 4,597,959 A | 7/1986 | Barr | |
| 4,678,516 A | 7/1987 | Alderman et al. | |
| 4,684,528 A | 8/1987 | Godfrey | |
| 4,758,439 A | 7/1988 | Godfrey | |
| 4,956,385 A | 9/1990 | Eby, III et al. | |
| RE33,465 E | 11/1990 | Eby, III et al. | |
| 5,002,970 A | 3/1991 | Eby et al. | |
| 5,030,459 A | 7/1991 | Barcelon et al. | |
| 5,059,416 A | 10/1991 | Cherukuri et al. | |
| 5,095,035 A | 3/1992 | Eby, III et al. | |
| 5,286,748 A | 2/1994 | Eby et al. | |
| 5,409,905 A | 4/1995 | Eby, III et al. | |
| 5,849,322 A | 12/1998 | Ebert et al. | |
| 5,955,097 A | 9/1999 | Tapolsky et al. | |
| 5,989,522 A | 11/1999 | Friedman | |
| 6,183,775 B1 * | 2/2001 | Ventouras | .................. 424/465 |
| 6,290,984 B1 | 9/2001 | Tapolsky et al. | |
| 6,316,008 B1 | 11/2001 | Godfrey | |
| 2002/0054917 A1 * | 5/2002 | Gohlke | ................. 424/535 |
| 2003/0003219 A1 * | 1/2003 | Day et al. | ................. 426/660 |
| 2003/0206942 A1 * | 11/2003 | Kulkarni et al. | .............. 424/443 |
| 2004/0086546 A1 * | 5/2004 | Maxwell et al. | .............. 424/439 |

FOREIGN PATENT DOCUMENTS

| | | |
|---|---|---|
| DE | 19856101 A1 | 8/2000 |
| WO | WO 97/40812 | 11/1997 |
| WO | WO 99/06030 | 2/1999 |
| WO | WO 99/17717 | 4/1999 |
| WO | WO 00/37044 | 6/2000 |
| WO | WO 01/03672 | 1/2001 |
| WO | WO 01/28570 | 4/2001 |

OTHER PUBLICATIONS

Dow, Dow Excipients, http://www.dow.com/dowexcipients/products/ethocel.htm, p. 1, 1995-2007.*
Merriam-Webster Online Dictionary, http://www.merriam-webster.com/dictionary/matrix, p. 1-2, 2008.*
Lin et al., "Micronized ethylcellulose used for designing a directly compressed time-controlled disintegration tablet" Journal of Controlled Release, 70, 321-328, Feb. 2001.*
Tisserand, The Art of Aromatherapy, p. 269, 1977.*

* cited by examiner

*Primary Examiner* — Lezah Roberts
(74) *Attorney, Agent, or Firm* — Shantnau Basu; Eckman Basu LLP

(57) ABSTRACT

Flavored dosage forms, e.g., lozenges and gums, are provided for sustained release of a flavoring agent in the mouth. The dosage forms provide sustained release by virtue of a wet matrix formed by admixture of a biocompatible, hydrophilic, water-insoluble polymer such as ethylcellulose and a flavoring agent, particularly an essential oil or a constituent thereof, e.g., a terpene or sesquiterpene. The dosage forms may also include a second beneficial agent in addition to the flavoring agent. Exemplary such beneficial agents include ionizable zinc compounds and other cold remedies, local anesthetic and anti-infective agents, diet aids, fluoride-releasing compounds, and nicotine. The dosage forms, when formulated as lozenges, may be somewhat adhesive or substantially non-tacky, depending primarily on the molecular weight of the hydrophilic polymer. Adhesive lozenges can serve as dosage forms that adhere to the teeth or gums for delivery of a beneficial agent thereto. Methods for using the dosage forms to provide sustained release of a flavoring agent and optionally deliver a second beneficial agent are also provided, as are methods for treating the common cold, treating a sore throat, facilitating weight loss, and assisting in smoking cessation.

18 Claims, No Drawings

LONG-LASTING, FLAVORED DOSAGE FORMS FOR SUSTAINED RELEASE OF BENEFICIAL AGENTS WITHIN THE MOUTH

CROSS-REFERENCE TO RELATED APPLICATIONS

This is a continuation-in-part of U.S. patent application Ser. No. 10/358,602, filed Feb. 4, 2003 now abandoned, the disclosure of which is incorporated by reference herein.

TECHNICAL FIELD

This invention relates generally to sustained release dosage forms, and more particularly relates to dosage forms that provide for sustained release of a flavoring agent over an extended time period. The invention additionally relates to such dosage forms that provide for sustained release of a beneficial agent in addition to a flavoring agent over the extended time period, and to various methods of use, including treatment of halitosis, treatment of the common cold, appetite suppression, and a method of achieving smoking cessation.

BACKGROUND

Systems that provide for sustained release of chemical compounds are useful in a host of contexts. Of particular interest herein are sustained release systems for providing gradual release of a beneficial pharmaceutical or other agent in the aqueous environment of the human body, specifically the mouth. The difficulty in achieving optimal sustained release systems for extended delivery of a beneficial agent in the mouth is that most such systems, e.g., lozenges, last for only a matter of minutes. For example, halitosis—commonly known as bad breath—is often treated with flavored lozenges and gums. Flavored lozenges and gums have also been used to deliver a pharmacologically active agent. For example, nicotine gums for assisting in smoking cessation are known and have been commercially available for some time. Most flavored lozenges, however, dissolve in several minutes or less, and therefore provide only a very short-term effect. Similarly, most gums tend to release substantially all of a beneficial agent (e.g., a flavoring agent or a pharmacologically active agent such as nicotine) in well under half an hour. Dosage forms for sustained release of beneficial agents in the mouth can be problematic in other respects as well. For example, commercially available zinc lozenges for treating the common cold tend to dissolve or degrade in well under 15 minutes, and, to the best of applicants' knowledge, no zinc lozenge has been disclosed as providing sustained release of zinc for over 40 minutes. Ideally, effective antiviral pharmacotherapy would involve a far longer time period during which the active agent is released from the lozenge.

Various materials and methods are used in the preparation of sustained release delivery systems. Often, sustained release is achieved by coating a dosage form such as a tablet or drug-containing core with a layer of a polymeric material that gradually hydrolyzes or erodes to release the beneficial agent within. Sustained release has also been achieved by granulating tablet materials with such a polymeric material. For instance, pharmaceutical grade ETHOCEL® brand ethylcellulose, available from the Dow Chemical Company (Midland, Mich.), is primarily used in the pharmaceutical industry to coat tablets and capsules, as granulation binders, and as binders in the direct compression of tablets. To date, however, neither ethylcellulose nor any other water-insoluble hydrophilic polymer as been used to provide a sustained release flavored dosage form as now disclosed.

There is, accordingly, a need in the art for a dosage form and method that achieve release of a beneficial agent in an aqueous environment, particularly in the mouth, over a sustained time period, preferably on the order of an hour or more. An ideal system would be a pleasantly flavored lozenge or gum that is comfortable to retain in the mouth for an extended period of time, provides effecting taste-masking of any bitter-tasting or otherwise unpleasant-tasting beneficial agents or excipients, can be easily manufactured, and can be used to deliver a wide variety of beneficial agents in the mouth. In addition, it would be optimal if the components of the composition could be varied only slightly to provide significant changes in properties and methods of use, e.g., to provide a non-adhesive lozenge or a relatively tacky dosage form that can adhere to the gum or teeth.

SUMMARY OF THE INVENTION

It is therefore a primary object of the invention to address the above-described need in the art by providing a dosage form and method that achieve sustained release of a beneficial agent in an aqueous environment such as the mouth for an extended time period.

In one embodiment, then, a flavored lozenge is provided that is composed of a sustained release wet matrix of ethylcellulose and a flavoring agent selected from essential oils, constituents of essential oils (e.g., terpenes and sesquiterpenes), and mixtures thereof. In an aqueous environment, particularly in the mouth, the matrix gradually releases the flavoring agent over a time period of at least 15 minutes and optimally up to four hours or more. Surprisingly, it has been found that the admixture of ethylcellulose with an essential oil, an individual terpene, or an individual sesquiterpene results in a wet matrix that provides for highly effective sustained release of an agent contained therein.

In another embodiment, a flavored lozenge is provided that is composed of at least one biocompatible, water-insoluble, hydrophilic polymer and a flavoring agent effective to provide a sustained release wet matrix upon admixture with the polymer(s), wherein the flavoring agent is as described above, i.e., selected from essential oils, constituents of essential oils, and mixtures thereof. In this embodiment, a preferred polymer is a polymer of lactic acid, in which case a water-soluble cellulosic polymer is preferably incorporated that provides the desired sustained release properties. The lactic acid polymer is either a poly(lactic acid) homopolymer or a copolymer of lactic acid, e.g., poly(lactide-co-glycolide). Here as well, the lozenge provides for sustained release of the flavoring agent in the mouth over a time period of at least 15 minutes and optimally up to four hours or more.

In either embodiment, at least one beneficial agent may be incorporated into the lozenge in addition to the flavoring agent, and the lozenge provides for sustained release of the beneficial agent as well. The lozenges are not limited with respect to the beneficial agent, except that the agent should be pharmaceutically acceptable and inert with respect to other components of the composition. Exemplary beneficial agents, however, include cold remedies, agents for combating halitosis, local anesthetics and anti-infective agents, diet aids, fluoride-releasing compounds and other agents exhibiting utility in the dental context, and nicotine. Zinc lozenges, for instance, are representative of those lozenges of the invention that can be used to treat colds and halitosis.

In an additional embodiment of the invention, the sustained release wet matrix of the biocompatible, water-insoluble, hydrophilic polymer and the flavoring agent is incorporated into a chewing gum base, such that the dosage form is a chewing gum that provides for sustained release of the flavoring agent. In addition to the flavoring agent within the wet matrix, one or more additional beneficial agents may, if desired, be incorporated into the chewing gum as well.

By varying the molecular weight of the hydrophilic polymer, and/or by incorporating an ingestible solvent such as ethanol or ethyl lactate, the lozenge may be rendered either adhesive or nonadhesive. That is, a lower molecular weight polymer will give rise to a sticky, pliable lozenge that can adhere to the gum, teeth, or dental appliance, while a higher molecular weight hydrophilic polymer will give rise to a soft, rubbery lozenge that is substantially nontacky. Incorporation of an ingestible solvent such as ethanol or ethyl lactate can further increase adhesion.

Methods are also provided for using the presently disclosed dosage forms in the administration of beneficial agents to the mouth of an individual, preferably a human individual. Administration may be local, such that the beneficial agent exhibits its desired effect within the oral cavity. Administration may also be systemic, in which case delivery of the beneficial agent is transmucosal, i.e., the beneficial agent passes through the mucosal lining of the oral cavity and into the bloodstream, such that the beneficial agent then exhibits its desired effect systemically. In one embodiment, the method provides for sustained release of a flavoring agent in the mouth, e.g., in the treatment of halitosis. In other specific embodiments, the following methods are provided:

a method for treating the common cold by administering to an individual in need of such treatment a flavored dosage form comprising an admixture of ethylcellulose having a solution viscosity in the range of approximately 6 to 49 cP as determined at 25° C. using a 5 wt. % aqueous solution, a flavoring agent selected from essential oils, individual terpenes, and individual sesquiterpenes, an ionizable zinc compound, a sweetening agent, wherein the weight ratio of the ethylcellulose to the flavoring agent is in the range of approximately 1:1.5 to 1.5:1;

a method for treating a sore throat, comprising administering to an individual in need of such treatment a flavored dosage form comprising an admixture of ethylcellulose having a solution viscosity in the range of approximately 6 to 49 cP as determined at 25° C. using a 5 wt. % aqueous solution, a flavoring agent selected from essential oils, individual terpenes, and individual sesquiterpenes, a local anesthetic agent, and a sweetening agent, wherein the weight ratio of the ethylcellulose to the flavoring agent is in the range of approximately 1:1.5 to 1.5:1;

a method for facilitating weight loss, comprising administering to an individual in need of such treatment a flavored dosage form comprising an admixture of ethylcellulose having a solution viscosity in the range of approximately 6 to 49 cP as determined at 25° C. using a 5 wt. % aqueous solution, a flavoring agent selected from essential oils, individual terpenes, and individual sesquiterpenes, a diet aid, and a non-sugar sweetening agent, wherein the weight ratio of the ethylcellulose to the flavoring agent is in the range of approximately 1:1.5 to 1.5:1; and a method for assisting an individual in quitting smoking, comprising administering to an individual in need of such treatment a flavored dosage form comprising an admixture of ethylcellulose having a solution viscosity in the range of approximately 6 to 49 cP as determined at 25° C. using a 5 wt. % aqueous solution, a flavoring agent selected from essential oils, individual terpenes, and individual sesquiterpenes, nicotine, and a sweetening agent, wherein the weight ratio of the ethylcellulose to the flavoring agent is in the range of approximately 1:1.5 to 1.5:1.

The lozenges of the invention are not only pleasantly flavored but also comfortable to retain in the mouth for an extended period of time, primarily by virtue of their small size and soft, rubbery consistency. Sustained release of a powerful flavoring agent within the lozenge provides for extremely effective taste-masking, and the lozenges can therefore be used to deliver a host of beneficial agents whose bitter or otherwise unpleasant taste has prevented administration in lozenge form.

In a further embodiment, a flavored dosage form is provided for delivering a beneficial agent to a mucosal surface within the mouth, the dosage form having at least one adhesive surface that serves to adhere the dosage form to the mucosal surface, and comprising ethylcellulose having a solution viscosity in the range of approximately 6 to 15 cP as determined at 25° C. using a 5 wt. % aqueous solution, a flavoring agent selected from essential oils, individual terpenes, and individual sesquiterpenes, a beneficial agent, and a sweetening agent, wherein the weight ratio of the ethylcellulose to the flavoring agent is in the range of approximately 1:1.5 to 1.5:1. The beneficial agent may be, for example, an anti-infective agent, a local anesthetic agent, or a local anti-inflammatory agent. The invention additionally encompasses a method for using the flavored dosage form to release the beneficial agent to the mucosal surface over an extended time period.

In another embodiment of the invention, a matrix of a biocompatible, water-insoluble, hydrophilic polymer, a flavoring agent, and a beneficial agent is incorporated into a dosage form such as a tablet, candy lozenge, gel, or gum, in order to mask the taste of the beneficial agent. In this embodiment, the polymer, flavoring agent, and beneficial agent are admixed to form a slurry, a particulate (e.g., powder) material such as xylitol, sorbitol, or the like is added to the slurry, and the slurry is further admixed to form a coated granulated matrix. The coated granulated matrix may be compacted into a tablet or other dosage form as is and/or admixed with other excipients prior to preparation of the final dosage form.

DETAILED DESCRIPTION OF THE PREFERRED EMBODIMENTS

Definitions, Nomenclature, and Overview:

Unless otherwise indicated, the invention is not limited to specific lozenge compositions, formulation components, or methods of manufacture, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a polymer" includes a single polymer as well as two or more polymers in combination, reference to "a flavoring agent" or "a colorant" encompasses a combination or mixture of different flavoring agents or colorants as well as a single flavoring agent or colorant, and the like.

In this specification and in the claims that follow, reference will be made to a number of terms, which shall be defined to have the following meanings:

"Optional" or "optionally present"—as in an "optional additive" or an "optionally present additive" means that the subsequently described component (e.g., additive) may or may not be present, so that the description includes instances where the component is present and instances where it is not.

By "pharmaceutically acceptable" is meant a material that is not biologically or otherwise undesirable, i.e., the material may be incorporated into a lozenge of the invention without causing any undesirable biological effects or interacting in a deleterious manner with any of the other components of the lozenge formulation. The term "biocompatible" is used interchangeably with the term "pharmaceutically acceptable." When the term "pharmaceutically acceptable" is used to refer to a pharmaceutical excipient, it is implied that the excipient has met the required standards of toxicological and manufacturing testing and/or that it is included on the Inactive Ingredient Guide prepared by the U.S. Food and Drug Administration.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of an adverse physiological condition in a susceptible individual as well as treatment of a clinically symptomatic individual by inhibiting or causing regression of the condition.

The term "beneficial agent" refers to any chemical compound, complex or composition that exhibits a beneficial effect, e.g., a therapeutic effect in the treatment of an adverse physiological condition. The term also encompasses pharmaceutically acceptable derivatives of those beneficial agents specifically mentioned herein, including, but not limited to, salts, esters, amides, prodrugs, active metabolites, isomers, analogs, and the like. When the term "beneficial agent" is used, then, or when a particular beneficial agent is specifically identified, it is to be understood that pharmaceutically acceptable, pharmacologically active salts, esters, amides, prodrugs, active metabolites, isomers, analogs, etc. of the beneficial agent are intended as well as the beneficial agent per se.

By an "effective" amount or a "therapeutically effective amount" of a beneficial agent is meant a nontoxic but sufficient amount of the agent to provide the desired effect. The amount of beneficial agent that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation The terms "hydrophilic" and "hydrophobic" are generally defined in terms of a partition coefficient P, which is the ratio of the equilibrium concentration of a compound in an organic phase to that in an aqueous phase. A hydrophilic compound has a P value less than 1.0, typically less than about 0.5, where P is the partition coefficient of the compound between octanol and water, while hydrophobic compounds will generally have a P greater than about 1.0, typically greater than about 5.0.

The term "water-insoluble" refers to a compound or composition whose solubility in water is less than 5 wt. %, preferably less than 3 wt. %, more preferably less than 1 wt. %, while the term "water-soluble" refers to a compound or composition whose solubility in water is greater than or equal to 5 wt. %, preferably greater than 10 wt. %, more preferably greater than 15 wt. % (measured in water at 20° C.).

Accordingly, the invention provides flavored dosage forms for release of a flavoring agent in the mouth, preferably sustained release over an extended time period. In one embodiment, the dosage form is a flavored lozenge that comprises a sustained release wet matrix of a biocompatible, water-insoluble hydrophilic polymer, e.g., ethylcellulose, a flavoring agent selected from essential oils, constituents of essential oils, and mixtures thereof, and, optionally, one or more additional beneficial agents, wherein, in an aqueous environment, the matrix gradually releases the flavoring agent and any other beneficial agent therein over a time period of at least 15 minutes, generally over a time period of at least 60 minutes, i.e., the length of time that an individually normally retains a lozenge in the mouth, but the lozenge is capable of providing sustained release over a time period of at least two, three, or even four or more hours. The lozenges of the invention do not dissolve within the mouth, but rather remain intact until removed by the user and/or until a substantial fraction of the flavoring agent has been released. In the latter case, release of a substantial fraction of the flavoring agent results in degradation of the wet matrix into small fragments that may or may not be swallowed, insofar as the entire dosage form is composed of biocompatible, nontoxic components.

The dosage form may also be a chewing gum composed of the aforementioned sustained release wet matrix and a gum base, wherein the gum base represents on the order of 5 wt. % to 90 wt. %, preferably about 5 wt. % to 50 wt. % of the gum. Any conventional gum base may be used, so long as there is no deleterious interaction between the gum base and the flavoring agent, the biocompatible polymer, or other components of the chewing gum. Typical gum bases include, by way of example, elastomers, elastomer plasticizers, waxes, fats, oils, softeners, emulsifiers, fillers, texturizers, and miscellaneous ingredients such as preservatives, colorants, whiteners, and the like. Most gum bases will include at least one elastomer, e.g., a synthetic elastomer such as polyisobutylene, polybutadiene, isobutylene-isoprene copolymer, styrene-butadiene copolymer, polyvinyl acetate, ethylene vinyl acetate, or polyvinyl alcohol, or a natural elastomer, including natural rubbers as well as natural gums (e.g., chicle). Typically, although not necessarily, the gum will be in the form of a tablet coated with a layer of a quickly dissolving colored or whitened film that provides a desirable appearance and smooth texture. Such film coatings are generally comprised of natural and/or synthetic hydrophilic polymers such as cellulosics, polyethylene glycol, and the like.

The length of time that the lozenge or gum can remain in the mouth and provide sustained release is controlled in part by the appropriate selection of hydrophilic polymer and flavoring agent, and in part by the relative amounts of the hydrophilic polymer and the flavoring agent. In general, the weight ratio of the hydrophilic polymer to the flavoring agent should be in the range of approximately 1:5 to 2:1, preferably in the range of approximately 1:2 to 1.5:1, and optimally in the range of approximately 1:1.5 to 1.2:1. A higher ratio of flavoring agent to polymer may provide a matrix that may be too sticky for some of the present purposes, while a lower ratio may result in a composition that is not sufficiently cohesive to provide the desired matrix, depending on the polymer and on other components of the composition. Accordingly, the aforementioned ratios are not intended to be limiting, however, and ratios outside of the recited ranges may be desirable to provide a different type of composition, e.g., compositions having a particularly soft consistency or a tendency to degrade more quickly.

Otherwise, the fraction of each component in the dosage form is not particularly important, although, typically, in a lozenge, the hydrophilic polymer and the flavoring agent each represents approximately 25-49.5 wt. % of the lozenge, and optional additives, e.g., added beneficial agents, sweeteners, and excipients typically represent about 1-50 wt. %, preferably about 1-45 wt. %, of the lozenge.

As may be surmised from the above description, the dosage forms of the invention are useful for the delivery of a beneficial agent to the teeth or a mucosal surface within the oral cavity. Delivery to a mucosal surface within the oral cavity may be used within the context of systemic drug administration, in which case the beneficial agent is actually delivered transmucosally, e.g., through the buccal mucosa of the gums. In this embodiment, the dosage form is composed of a wet matrix as described above with regard to sustained release lozenges, but is formulated so as to have a surface that is sufficiently tacky to enable the dosage form to adhere to the teeth or a mucosal surface within the mouth. This may be accomplished by using a relatively low molecular weight biocompatible polymer, as discussed infra, and/or by incorporating one or more adhesive polymers that are conventionally used in buccal drug delivery systems, e.g., polyisobutylene, polyisoprene, acrylic acid polymers and copolymers (e.g., those known as "carbomers," polyalkylene oxides (e.g., polyethylene glycol and copolymers thereof), polyvinyl lactams (e.g., polyvinyl pyrrolidone), and cellulosic materials (e.g., hydroxypropylmethyl cellulose). Preferably, the dosage form is made adhesive by using a lower molecular weight hydrophilic polymer rather than by incorporation of additional polymers not contained within the wet matrix. When the dosage forms of the invention serve as transmucosal delivery systems, various carriers and additives may be incorporated as is well known in the art of transmucosal (e.g., buccal) drug delivery. Typical additives include permeation enhancers such as polyethylene glycol esters, long-chain fatty acid esters of diols and triols (e.g., glycerol monolaurate, propylene glycol monolaurate), lower alkanols, and the like.

The Hydrophilic Polymer:

The hydrophilic polymer is both water-insoluble and biocompatible as those terms are defined herein. That is, the polymer component of the dosage form has: an octanol-water partition coefficient P of less than 1.0, preferably less than 0.5; a solubility in water of less than 5 wt. %, preferably less than 3 wt. %, most preferably less than 1 wt. % at 0° C.; and does not give rise to undesirable biological effects or interact in an adverse manner with any of the other components of the dosage form. Preferred polymers within this group may be identified by wetting a candidate polymer with a flavoring agent such as an essential oil or terpene as described infra to form a wet polymer matrix, compressing the wet matrix (such that the polymer dissolves to some extent in the essential oil or terpene), and noting the consistency of the compressed matrix. Ideal polymers result in a compressed wet matrix that has a rubbery consistency and exhibits both physical integrity and some degree of porosity.

When the dosage form is a lozenge, varying the molecular weight or viscosity of the polymer can impart certain properties to the dosage form. More specifically, a lower molecular weight polymer (e.g., ethylcellulose having a solution viscosity of about 6 to 15 cP) can give rise to a pliable, sticky lozenge, as alluded to in the preceding section, while a higher molecular weight polymer can provide a soft, rubbery, and nontacky lozenge. Molecular weight also impacts on release rate and time to disintegration in the mouth, i.e., on the rate at which flavoring agent and/or other components in the dosage form are released and on the time the dosage form remains intact, respectively. With a chewing gum, for example, a higher molecular weight polymer results in a gum that lasts longer than a gum prepared with a lower molecular weight polymer but that is otherwise identical. With lozenges, use of a higher molecular weight polymer, as compared to a lower molecular weight polymer, tends to give rise to a product that exhibits more rapid release kinetics and more rapid breakdown (see Example 15), given an equivalent amount of other components present. It should be noted that using a lower molecular weight polymer enables the incorporation of a smaller fraction of essential oil or terpene without reducing the overall strength of the matrix.

The particle size of the polymer is also relevant to the properties of the dosage forms made therewith. Generally, the polymers useful in conjunction with the invention have a particle size in the range of about 1 micron to about 250 microns. Micronized polymers, e.g., micronized ethylcellulose, are preferred for formation of strong polymer matrix systems, while matrices manufactured with polymers having a larger particle size tend to break apart faster. Micronized polymers generally have a particle size of less than 75 microns, with a mean of about 20 microns, and a typical size range in the range of about 1 micron to about 50 microns.

For the present purpose, an exemplary cellulosic polymer is ethylcellulose. The ethylcellulose should have a solution viscosity in the range of approximately 1 to 120 cP, with a preferred solution viscosity in the range of approximately 3 to 100 cP, and a most preferred solution viscosity in the range of approximately 6 to 49 cP. The ethoxyl content is typically in the range of about 45.0% to 52.0%, preferably in the range of about 48.0-49.5%. Suitable ethylcellulose polymers that are available commercially include, without limitation, those that may be obtained from the Dow Chemical Company (Midland, Mich.) as ETHOCEL® ethylcellulose, e.g., ETHOCEL® Standard 4 Premium (solution viscosity range approximately 3 to 5.5 cP, ethoxyl content 48.0-49.5%), ETHOCEL® Standard 7 Premium (solution viscosity range approximately 6 to 8 cP, ethoxyl content 48.0-49.5%), ETHOCEL® Standard 10 Premium (solution viscosity range approximately 9 to 11 cP, ethoxyl content 48.0-49.5%), ETHOCEL® Standard 14 Premium (solution viscosity range approximately 12.6 to 15.4 cP, ethoxyl content 48.0-49.5%), ETHOCEL® Standard 20 Premium (solution viscosity range approximately 18 to 22 cP, ethoxyl content 48.0-49.5%), ETHOCEL® Standard 45 Premium (solution viscosity range approximately 41 to 49 cP, ethoxyl content 48.0-49.5%), ETHOCEL® Standard 100 Premium (solution viscosity range approximately 90 to 110 cP, ethoxyl content 48.0-49.5%), ETHOCEL® Medium 50 (solution viscosity range approximately 43 to 55 cP, ethoxyl content 45.0-47.0%), ETHOCEL® Medium 70 (solution viscosity range approximately 63 to 85 cP, ethoxyl content 45.0-47.0%), ETHOCEL® Medium 100 (solution viscosity range approximately 90 to 110 cP, ethoxyl content 45.0-47.0%), and ETHOCEL® HE 10 (solution viscosity range approximately 9 to 11 cP, ethoxyl content 49.5-52.0%), with all solution viscosities determined using an Ubbelohde viscometer and a solvent mixture of 80% toluene and 20% alcohol.

Other suitable biocompatible polymers are lactic acid polymers. The lactic acid polymer may be a homopolymer or a copolymer, if a copolymer, typically a copolymer with glycolic acid, also termed "poly(lactide-co-glycolide." The lactic acid in these polymers may be in enantiomerically pure form, as D-lactic acid or L-lactic acid, or it may be in the form of a racemic mixture of the two enantiomers. Accordingly, these polymers include poly(D,L-lactic acid), poly(D-lactic acid), poly(L-lactic acid), poly(D,L-lactide-co-glycolide), poly(D-lactide-co-glycolide), and poly(L-lactide-co-glycolide). Suitable lactic acid polymers and copolymers will generally have a number average molecular weight $M_n$ in the range of approximately 10,000 to 125,000. With poly(lactide-co-glycolide) polymers, the amount of glycolic acid in the copolymer should not exceed 50 mole %. Any poly(lactide-co-glycolide) selected as the hydrophilic polymer will typically contain approximately 1 mole % to 50 mole %, preferably approximately 15 mole % to 50 mole %, and most preferably approximately 15 mole % to 35 mole %, glycolic acid. The cellulosic polymer can be any such polymer capable of rendering the lactic acid polymer suitable for sustained release in the context of the invention.

In this embodiment, when the hydrophilic polymer is a lactic acid polymer, a release rate accelerator should be used. Suitable release rate accelerators, as discussed infra, include water-soluble cellulosic polymers such as methylcellulose (MC), hydroxypropyl cellulose (HPC), and hydroxypropyl methylcellulose (HPMC), and ingestible organic solvents such as ethyl acetate and ethanol. The weight ratio of release rate accelerator to the lactic acid polymer is generally in the range of about 0.05:1 to 0.5:1, typically about 0.1:1 to 0.5:1. If desired, release rate modifiers such as these may also be used in conjunction with ethylcellulose, in order to adjust the duration of the time period over which the flavoring agent and optionally other agent(s) are released.

The Flavoring Agent:

A wide range of flavoring agents is available and may be used as a component of the wet matrix in the dosage forms described herein. Flavoring agents may be combined, if desired, to produce a particular flavor mix. Preferred flavoring agents are those that upon admixture with the hydrophilic polymer result in a wet matrix that, in an aqueous environment (e.g., in the mouth) gradually releases the flavoring agent and any other incorporated component. By a "wet" matrix is meant a matrix that contains a liquid phase that represents a sufficiently large fraction of the matrix to provide a discernibly wet or sticky surface, and/or a soft and rubbery consistency. Ideal flavoring agents in this regard are pharmaceutically acceptable essential oils and chemical constituents of essential oils that can impart a desired flavor. Essential oils, as known in the art, are naturally occurring compounds or compositions that accumulate in the oil cells, glandular trichomes, and oil or resin ducts of aromatic plants.

Essential oils that can be incorporated into the present flavored dosage forms as suitable flavoring agents include, without limitation, citrus oils such as lemon oil, lime oil, neroli oil, and orange oil, mint oils such as peppermint oil and spearmint oil, and other oils such as anise oil, cardamom oil, cinnamon oil, clove oil, coriander oil, eriodictyon fluidextract, eucalyptus oil, fennel oil, glycyrrhiza extract, lemongrass oil, and nutmeg oil. The citrus and mint oils are generally preferred.

As is widely appreciated in the art, essential oils contain a number of constituents, many of which can by themselves serve as flavoring agents. Of these, the most well-known essential oil constituents that are widely used as flavoring agents are hydrocarbons, particularly terpenes and sesquiterpenes. "Terpenes" generally refer to hydrocarbons of the formula $C_{10}H_{16}$, and, as the term is used herein, also encompass terpene analogs of the formula $C_nH_{2n-4}$, as well as terpenes and terpene analogs substituted with one or more non-hydrogen substituents and/or containing a heteroatom such as N, O, or S. Analogously, "sesquiterpenes" generally refer to hydrocarbons of the formula $C_{15}H_{24}$, but for the purpose of the present invention also encompass sesquiterpene analogs of the formula $C_nH_{2n-6}$ as well as substituted and/or heteroatom-containing derivatives thereof.

It will be appreciated from the foregoing definitions that terpenes and sesquiterpenes can have any number of molecular structures, including acyclic, monocyclic, bicyclic, and polycyclic structures, wherein the bicyclic and polycyclic structures may or may not be "bridged" bicyclic and polycyclic compounds. In general, however, the terpenes that are more commonly used as flavoring agents contain two double bonds and one cyclic group (e.g., β-phellandrene) or one double bond and two cyclic groups in a bridged bicyclic structure (e.g., β-pinene). Specific examples of terpenes and sesquiterpenes that can be advantageously used as flavoring agents herein include: the terpenes d,l-camphene, d-camphene, l-camphene, $\Delta^3$-carene, trans-β-ocimene, cis-β-ocimene, trans-α-ocimene, cis-α-ocimene, β-pinene, β-phellandrene, α-terpinene, β-terpinene, and γ-terpinene; and the sesquiterpenes α-cadinene, β-cadinene, α-caryophyllene, copaene, β-farnesene, isocaryophyllene, and ylangene.

In addition to the terpenes and sesquiterpenes, essential oils contain a number of other types of constituents that may also serve as flavoring agents, either individually or in combination. These include, by way of example:

organic acids such as p-anisic acid, cinnamic acid, and phenylacetic acid;

alcohols, including phenols, such as d,l-borneol, d-borneol, l-borneol, carvacrol, chavicol, cinnamyl alcohol, linalool, menthol, nerolidol, nerol, d,l-α-terpineol, d-α-terpineol, l-α-terpineol, and thymol;

aldehydes such as acetaldehyde, anisaldehyde, cinnamaldehyde, benzaldehyde, citral, isovaleric aldehyde, piperonal, salicylaldehyde, valeric aldehyde, and vanillin;

ketones such as carvone, jasmone, menthone, and piperitone;

esters such as amyl acetate, bornyl acetate, benzyl benzoate, butyl cinnamate, cinnamyl anthranilate, geranyl acetate, linalyl acetate, menthyl acetate, menthyl isovalerate, and methyl salicylate; and phenol ethers such as anethole, eugenol, safrol, and estragole.

The choice of flavoring agent will depend, in part, upon the intended use of the dosage form. In the treatment of halitosis, for example, mint oils such as peppermint oil and spearmint oil are generally preferred. As another example, dosage forms designed as diet aids may contain food flavors (e.g., citrus oils or the like) so as to satisfy the need for the taste of food in the mouth.

The amount of flavoring agent used can be varied in order regulate the strength of the polymeric matrix prepared. Higher levels of the essential oil, terpene, or the like relative to the matrix polymer will give rise to a stronger, more cohesive matrix and thus a slower release rate.

Sweeteners, Colorants, and Other Additives:

In order to enhance the taste of the dosage form, at least one sweetener is preferably incorporated into the formulation. The sweetener may be a sugar, e.g., sucrose, fructose, or dextrose, or, more preferably, a non-sugar sweetening agent to reduce both caloric intake and the likelihood of dental caries. Sweeteners falling within the latter group include many well known artificial sweetening agents, such as, for instance, aspartame, saccharin, saccharin salts (e.g., sodium saccharin, calcium saccharin), sucralose, acesulfame-K (potassium acetosulfam), sorbitol, xylitol, stevioside, steviol, mannitol, erythritol, lactitol, alitame, miraculin, monellin, and thaumatin. In lozenges of the invention, the sweetener is generally incorporated within the wet matrix, i.e., physically entrapped therein, while when the dosage form is a gum, this is not generally the case. That is, with gums, although the sweetener and the wet matrix may be intimately mixed, the sweetener is not entrapped within the gum (although this tends to result in quicker release of the sweetener from a gum than a lozenge, the release of the flavoring agent is gradual in all dosage forms of the invention).

The dosage form optionally contains a colorant and/or other conventional additives as well. With respect to colorants, some essential oils are already colored and the color so provided may be acceptable. For example, peppermint oil imparts a yellow color, while cinnamon oil imparts a brown color.

Without an added colorant, and in the absence of a colored flavoring agent, the lozenges and gums of the present invention will tend to be off-white or slightly darker, and may have some degree of translucence. Accordingly, a colorant must be added if a colored dosage form is desired. Suitable colorants include natural colorants, i.e., pigments and dyes obtained from mineral, plant, and animal sources. Examples of natural colorants include red ferric oxide, yellow ferric oxide, annattenes, alizarin, indigo, rutin, and quercetin. Synthetic colorants may also be used, and will typically be an FD&C or D&C dye, e.g., an approved dye selected from the so-called "coal-tar" dyes, such as a nitroso dye, a nitro dye, an azo dye, an oxazine, a thiazine, a pyrazolone, a xanthene, an indigoid, an anthraquinone, an acridine, a rosaniline, a phthalein, a quinoline, or a "lake" thereof, i.e., an aluminum or calcium salt thereof. Particularly preferred colorants are food colorants in the "GRAS" (Generally Regarded As Safe) category.

Other optional additives include, for example:

release rate modifiers, particularly release rate accelerants that also serve as softening agents, such as water-soluble polymers (e.g., MC, HPC, HPMC, etc.) and ingestible solvents (e.g., ethyl acetate, ethanol, glycerol, glycerol esters, etc.);

adhesion modifiers (including adhesion-increasing agents and adhesion-reducing agents) such as ingestible solvents (e.g., ethyl acetate and ethanol increase tack when admixed with ethylcellulose), mineral oil and vegetable oils (which tend to decrease tack when admixed with ethylcellulose), and additional polymers and polymer compositions, including polymers typically used to form hydrogels, e.g., ethylene vinyl acetate, polyvinyl alcohol, polyvinyl pyrrolidone, cellulose acetate, cellulose diacetate, and other cellulose esters, which may increase or decrease tack depending on the particular polymer or polymer composition;

flavor stabilizers (e.g., starches);

flavor diluents (e.g., ingestible solvents, as above);

pH-adjusting agents (e.g., acids, bases, buffer systems);

preservatives (e.g., antioxidants, antimicrobial agents, etc.);

binders to increase cohesiveness and promote more gradual erosion of the dosage form (e.g., polycarbophil, polyethylene oxide, gum arabic, stearic acid);

disintegrants for use in preparing quickly releasing and disintegrating dosage forms (e.g., glycerol, sugars, other polyols, etc.);

lubricants;

fillers (e.g., maltodextrin, microcrystalline cellulose, lactose, mannitol, etc.); and enhancers to increase permeation of beneficial agent(s) into the tissues of the oral cavity (e.g., in the administration of anti-inflammatory and/or antibiotic agents to treat oral mucositis, cold sores, periodontal disease, and pain following surgeries of the oral cavity or gums) and/or through the oral mucosa and into the bloodstream, to achieve enhanced systemic levels of a beneficial agent (as in sublingual drug administration) that has low oral bioavailability and does not readily penetrate through mucosal tissue. Methyl sulfonyl methane ("MSM") represents a preferred enhancer.

It will be appreciated that certain compounds can serve at least one purpose; for example, an ingestible solvent can serve as both a release rate modifier and flavor diluent.

Other Beneficial Agents:

In addition to the flavoring agent, the dosage form may also include one or more beneficial agents that are released within the mouth. Lozenges of the invention will provide for sustained release of additional beneficial agents because the agents are incorporated within the wet matrix composed of the hydrophilic polymer and the flavoring agent. With gums, release of an added beneficial agent may or may not be gradual, since the added agent will generally not be incorporated into the aforementioned wet matrix; rather, the release profile will depend on factors such as the nature of the agent(s), the tendency of the agent to remain in the dosage form (i.e., the physical/chemical attraction of the agent to one or more components of the gum), and the presence of one or more sustained release polymers.

The appropriate amount of any beneficial agent in the dosage form will depend on the particular agent and the intended daily dose, and presumes that one to six, generally two to four, dosage forms will be consumed on a daily basis. Unless explicitly indicated herein, it is to be understood that appropriate daily doses for the various agents will be known to those of ordinary skill in the art of pharmaceutical formulation and pharmacology and/or can be found in the pertinent texts and literature.

The beneficial agent may be administered to provide a local, topical effect, within the oral cavity (e.g., as a topical anti-infective or anesthetic), or to achieve a systemic effect by passing through the mucosal membranes within the oral cavity and into an individual's blood stream. The beneficial agents that may be delivered using the dosage forms of the invention are not limited, as the invention enables the effective delivery of a wide variety of beneficial agents. Therefore, the beneficial agent administered may be selected from any of the various classes of such agents including, but not limited to, analgesic agents, anesthetic agents (including local anesthetic agents for numbing a painful region within the mouth), anti-anginal agents, antiarthritic agents, anti-arrhythmic agents, antiasthmatic agents, anti-BPH agents, anticancer agents, anticholinergic agents, anticoagulants, anticonvulsants, antidepressants, antidiabetic agents, antidiarrheals, anti-epileptic agents, antifungal agents, antigout agents, antihelminthic agents, antihistamines, antihypertensive agents, antiinflammatory agents, antimalarial agents, antimicrobial agents (including local antibiotics for treatment of an infection of the gum or elsewhere within the oral cavity), antimigraine agents, antimuscarinic agents, antinauseants, antineoplastic agents, antiosteoporosis agents, antiparkinsonism agents, antiprotozoal agents, antipruritics, antipsychotic agents, antipyretics, antispasmodics, antithyroid agents, antitubercular agents, antiulcer agents, anti-urinary incontinence agents, antiviral agents, anxiolytics, attention deficit disorder (ADD) and attention deficit hyperactivity disorder (ADHD) drugs, calcium channel blockers, cardiac inotropic agents, beta-blockers, central nervous system stimulants, cognition enhancers, corticosteroids, COX-2 inhibitors, cough and cold preparations, diet aids, diuretics, gastrointestinal agents, genetic materials, histamine receptor antagonists, hormonolytics, hypnotics, hypoglycemic agents, immunosuppressants, keratolytics, leukotriene inhibitors, lipid-regulating agents, macrolides, mitotic inhibitors, muscle relaxants, narcotic antagonists, neuroleptic agents, nicotine, nutritional agents, such as vitamins, essential amino acids, and fatty acids; parasympatholytic agents, sedatives, sex hormones, sympathomimetic agents, tranquilizers, vasodilators, vitamins, and combinations thereof.

Any of the aforementioned active agents may also be administered in combination using the present formulations.

Active agents administered in combination may be from the same therapeutic class (e.g., two different diet aids) or from different therapeutic classes (e.g., a decongestant and a vitamin). Some agents, as will be appreciated by those of ordinary skill in the art, are encompassed by two or more of the aforementioned groups.

The dosage forms of the invention are well-suited to administer beneficial agents whose efficacy increases as a result of an extended residence time in the oral cavity, which results in greater oral mucosal absorption of any particular agent. Such agents include, by way of example: glutathione and other agents that are degraded in or otherwise rendered unstable in the gastrointestinal tract; coenzyme Q10 and xylitol, in the treatment of periodontal disease and/or adverse systemic conditions; aspirin and nonsteroidal anti-inflammatory agents; antinauseants, anti-emetic agents, opioid analgesics, and other medications which the stomach may not tolerate (and, therefore, have had to be administered rectally or via some other relatively inconvenient non-oral route of administration); and allergy medications for rapid relief of allergic symptoms (e.g., diphenhydramine).

The present dosage forms are also useful in pediatric applications, i.e., in the administration of cough and cold medications to children. In this way, the need for medicated tablets, which children often find difficult to swallow, is avoided.

Beneficial agents of particular interest herein are cold remedies, agents for combating halitosis, local anesthetics, local anti-infective agents, diet aids, fluoride-releasing compounds and other agents exhibiting utility in the dental context, and nicotine.

Cold remedies include, but are not limited to: sources of $Zn^{2+}$, i.e., ionizable zinc compounds; vitamins, including vitamin C optionally combined with one or more B vitamins; and herbal extracts such as echinacea and golden seal.

Ionizable zinc compounds are useful for reducing the duration and/or symptoms of common colds, managing upper respiratory allergy, as nutritional agents, and in treating halitosis, i.e., for reducing or eliminating bad breath. The ionizable zinc compound may be an inorganic or organic complex; examples of suitable complexes include zinc gluconate, acetate, chloride, propionate, butyrate, n-butyrate, beta-hydroxybutyrate, benzoate, formate, and sulfate, although zinc acetate and gluconate are generally preferred for reasons of stability, acidity in an aqueous environment (and thus potential toxicity), and suitability for sustained release in the present formulations. In this embodiment, lozenges are preferred to gums, so as to maximize the time period during which the zinc compound is released. The wet matrix of the present dosage forms, which provides for gradual release of a flavoring agent in the mouth, also serves to minimize the unpleasant, bitter taste of many zinc-containing compounds. In addition, conventional zinc lozenges last only minutes, so that the availability of zinc in the mouth is limited, which correspondingly limits the capability of the zinc to exert a maximal antiviral effect. Generally, the amount of ionic zinc (i.e., $Zn^{2+}$) in a dosage form of the invention is in the range of about 1 mg to about 50 mg, typically in the range of about 5 mg to about 40 mg, preferably in the range of about 15 mg to about 35 mg (these ranges correspond to about 12.8 mg to about 640 mg, typically about 64 mg to about 512, preferably about 192 mg to about 448 mg zinc gluconate, insofar as ionic zinc represents approximately 12.8 wt. % of zinc gluconate).

For the treatment of colds, combinations of ionizable zinc compounds with other cold remedies, e.g., vitamin C, herbal remedies, decongestants, etc., are particularly desirable.

In treatment of halitosis, the dosage forms do not require a beneficial agent, insofar as the flavoring agent itself reduces bad breath for extended time periods. Incorporation of an additional beneficial agent such as an ionizable zinc compound, however, can also serve to combat halitosis. While the flavoring agent masks the odor associated with halitosis, a zinc compound as discussed above, such as zinc acetate or zinc gluconate, acts in a different manner, by combining with the volatile sulfur compounds that produce halitosis. Other agents for reducing or eliminating halitosis can also be incorporated into the dosage form, and may or may not target a particular cause of the problem (e.g., infections of the mouth, nasal or sinus conditions, gastrointestinal disorders, diabetes, etc.). For example, anti-infective agents such as triclosan or phenol may be suitable. In contrast to breath mints and other breath fresheners known in the art, the present dosage forms, containing a flavoring agent and optionally one or more additional beneficial agents for treating halitosis, can reduce bad breath for up to several hours or more. With non-sugar sweeteners, the dosage form does not promote dental caries, while nevertheless retaining a pleasant, sweet taste for an extended time period.

In a related embodiment, the dosage forms may contain a local anesthetic agent to reduce sore throat pain, and/or a local anti-infective agent to eliminate any bacteria or virii associated with the sore throat. Local anesthetics include, for example, menthol, benzocaine, bupivacaine, butambenpicrate, chlorprocaine, cocaine, dibucaine, dimethisoquin, dyclonine, etidocaine, hexylcaine, hexylresorcinol, ketarine, lidocaine, mepivacaine, phenol, phenolate, pramoxine, procaine, ropavacaine, tetracaine, tripelennamine, xylocaine, and pharmaceutically acceptable salts thereof (e.g., dimethisoquin hydrochloride, pramoxine hydrochloride) while representative anti-infective agents include amylmetacresol, benzalkonium, cetylpyridinium, chlorhexidine, dequilinium, domiphen, dichlorobenzyl alcohol, phenol, and tyrothicin. Of course, a source of zinc ion such as zinc acetate or zinc gluconate can also be incorporated into a lozenge or gum for reducing sore throat pain, insofar as such compounds exhibit antiviral activity as noted above. It will be appreciated that these dosage forms are also useful in treating and/or reducing pain associated with local viruses of the mouth, which are often manifested as sores or lesions (e.g., those associated with herpes infection), or with various disorders of the tongue.

The dosage forms of the invention are also useful in treating oral sores, including cold sores and oral mucositis. Use of anti-inflammatory agents and antibiotics to treat or prevent cold sores and oral mucositis has, in the past, proven difficult because ointments and mouth washes result in limited contact of the agent with the affected tissue. By contrast, the dosage forms of the invention can provide extended contact of the beneficial agent (e.g., dexamethasone) with the affected tissue, and thereby reduce the length of time required for a sore to heal. In the treatment of oral sores, a local anesthetic agent as those enumerated above may also be advantageously incorporated into a dosage form of the invention.

The present dosage forms additionally exhibit utility in facilitating weight reduction, insofar as the sustained release of flavor mimics the taste of food in the mouth, particular when the flavoring agent is a food flavor, e.g., a citrus oil or the like. Incorporation of a diet aid, however, will increase the utility of the dosage forms in this regard. Diet aids include any agents that assist an individual to reduce the intake of food, regardless of mechanism. Therefore, diet aids for use herein may suppress appetite, give the feeling of "fullness," and/or increase metabolism. While any diet aid may be administered to an individual using the present dosage forms, exemplary diet aids include 5-hydroxytryptophan, tyrosine, phenylalanine, pseudoephedrine, ephedrine, phenylpropanolamine, chromium picolinate, aspirin, benzocaine, carnitine, and caffeine. Certain herbal preparations, mixtures, and extracts are also suitable diet aids, and include, without limitation, guarana and ma huang.

In another embodiment, the beneficial agent is one that promotes healthy teeth and gums, or that exhibits other utility in the "dental" context. For instance, a fluoride-releasing dosage form may be prepared by incorporating a source of fluoride ion as a beneficial agent. Fluoride-releasing agents are well known and include sodium monofluorophosphate, sodium fluoride, and stannous fluoride. Fluoride-containing dosage forms preferably contain xylitol as a sweetener, as xylitol may potentiate the action of the fluoride. Also, a local anesthetic agent, as described above, can provide for desensitization within the mouth, to alleviate a toothache, pain associated with a condition or disorder of the gums, or the pain or discomfort that may follow a dental procedure.

Another beneficial agent is nicotine, which may be in the form of the free base or an acid addition salt thereof. As an aid to smoking cessation, nicotine has been incorporated into gums and other drug delivery systems in the form of the acid addition salt, in large part to offset the bitter and unpleasant taste of the free base. Because the flavored matrix of the present dosage forms provides for very effective taste-masking with respect to a wide variety of beneficial agents, however, nicotine can be incorporated and released as the free base. Since the base is more readily delivered across the mucosal membrane than the salt form of the drug, the invention enables delivery of a lower dose of nicotine, particularly when the dosage form is a lozenge. Preferred gums and lozenges contain 2 mg, 4 mg, or 10 mg nicotine. That is, a lozenge of the invention can contain less than about 5 mg of nicotine, typically 0.1 to 2 mg, preferably 0.25 to 1.5 mg, while nevertheless providing the desired therapeutic effect. With nicotine-containing dosage forms, it may be desirable to incorporate or disperse the nicotine in an excipient that reduces the volatility of the drug (e.g., mannitol, microcrystalline cellulose, colloidal silica), unless the nicotine is in the form of an acid addition salt. Also, a sweetener is virtually essential to provide taste-masking. While any of the above-mentioned sweeteners may be used, a particularly preferred sweetener in nicotine lozenges is sucralose.

While the above discussion refers to certain dosage forms of the invention as "lozenges," it is to be understood that the term encompasses lozenge-type dosage forms having some degree of adhesion. Such dosage forms are generally substantially flat and adhere to the gum or teeth to deliver a beneficial agent, e.g., an anti-infective agent including any of the local anti-infective agents set forth above, a local anesthetic agent, including those exemplified previously, or an anti-inflammatory agent. Anti-inflammatory agents include NSAIDS (non-steroidal anti-inflammatory agents) such as ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen and tiaprofenic acid; acetylsalicylic acid, apazone, diclofenac, difenpiramide, diflunisal, etodolac, flufenamic acid, indomethacin, ketorolac, meclofenamate, mefenamic acid, nabumetone, phenylbutazone, piroxicam, sulindac, and tolmetin, and corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, methylprednisolone, clobetasol, betamethasone fluocinonide, mometasone, triamcinolone acetonide, and the like.

Any of the beneficial agents may be in the form of a salt, ester, amide, prodrug, active metabolite, isomer, analog, or the like, provided that the salt, ester, amide, prodrug, active metabolite, isomer, or analog is pharmaceutically acceptable and retains at least some degree of the desired activity. Salts, esters, amides, prodrugs, metabolites, analogs, and other derivatives of the beneficial agents herein may be prepared using standard procedures known to those skilled in the art of synthetic organic chemistry and described, for example, by J. March, Advanced Organic Chemistry: Reactions, Mechanisms and Structure, 4th Edition (New York: Wiley-Interscience, 1992).

For example, acid addition salts are prepared from a beneficial agent in the form of a free base using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties that may be present on an active agent may be carried out in a similar manner using a pharmaceutically acceptable base such as sodium hydroxide, potassium hydroxide, ammonium hydroxide, calcium hydroxide, trimethylamine, or the like. Preparation of esters involves transformation of a carboxylic acid group via a conventional esterification reaction involving nucleophilic attack of an $RO^-$ moiety at the carbonyl carbon. Esters can be reconverted to the free acids, if desired, by using conventional hydrogenolysis or hydrolysis procedures. Amides may be prepared from esters, using suitable amine reactants, or they may be prepared from an anhydride or an acid chloride by reaction with ammonia or a lower alkyl amine. Prodrugs and active metabolites may also be prepared using techniques known to those skilled in the art or described in the pertinent literature. Prodrugs are typically prepared by covalent attachment of a moiety that results in a compound that is therapeutically inactive until modified by an individual's metabolic system.

Other derivatives and analogs of the beneficial agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

Methods of Manufacture and Use:

The lozenges are prepared by admixture of the hydrophilic polymer and the flavoring agent and any additional components, including sweeteners, colorants, other additives discussed herein, and additional beneficial agents. Admixture can generally be carried out at room temperature and ambient humidity, unless a particular beneficial agent or other component of the lozenge requires a protected environment, a lower temperature, or lower humidity. Using the appropriate weight ratio of the hydrophilic polymer to the flavoring agent as discussed supra, admixture of the components results in a pliable wet matrix that can be formed into a roll or sheet. After allowing the composition to set, typically over a 24-hour period, the lozenges are then created by cutting of the roll or die cutting of the sheet. In a preferred embodiment, the mixture of the components is compressed to form lozenges. For example, the mixture can be compressed in a two-part lozenge-shaped mold, wherein after the mixture is added to a recess within the lower half of the mold, the upper half is aligned therewith and pressure is applied to compress the mixture. Compressed lozenges can be made so as to remain intact within the mouth for extended time periods, on the order of five hours or more. It will be appreciated, however, that the present process can be tailored to provide compressed lozenges that degrade more quickly, for example by varying the proportion of flavoring agent(s) and/or excipients.

If a somewhat tacky lozenge is desired, e.g., a dosage form that adheres to the buccal mucosa for delivery of a beneficial agent, the same procedures are followed except that a lower molecular weight hydrophilic polymer is used to impart adhesive strength to the lozenge by virtue of the tacky surface provided. Alternatively, or in addition, one or more adhesive polymers can be incorporated into the lozenge formulation to provide the desired degree of adhesion, as described elsewhere herein.

Chewing gums may be prepared by first formulating the wet matrix as described above, i.e., by admixing the hydrophilic polymer and the flavoring agent. Then, the matrix, along with any additional components, e.g., sweeteners, colorants, or other additives, is admixed with a selected chewing gum base as described earlier herein. Mixing may be effected using any suitable mixing device, e.g., a ribbon blender. The resultant chewing gum is then manufactured into strips or tablets of a desired size.

The dosage forms so prepared are individually packaged in a manner that promotes shelf life and maximizes the stability of the flavoring agent. These requirements translate into a package design in which both the air space and exposed surface area of the lozenge are minimized, and in which the packaging material used has very low permeability to vapor. A plastic-lined foil, wherein the plastic is a low permeability material, is optimal. Ideally, the packaging material should be in contact with at least 85% of the surface of the lozenge to minimize loss of flavor, and packaging materials that do not transmit organic vapors are optimal. For example, polyolefinic materials such as poly(vinylidene chloride), polyethylene (including low density and higher density polyethylenes), polypropylene, and copolymers thereof represent suitable packaging materials.

The dosage forms of the invention may be prepared in any number of shapes and sizes, and the invention is not limited in this regard. Different shapes and sizes may be desirable for different applications. Typical dimensions, however, are on the order of 0.4"×0.5"×0.2" for lozenges, while lozenge weight is generally in the range of about 0.4 to 0.8 g. For chewing gums, the dimensions will generally be somewhat different, insofar as flat, elongated strips and/or larger tablets are often preferred.

It is to be understood that while the invention has been described in conjunction with the preferred specific embodiments thereof, the description above as well as the examples that follow are intended to illustrate and not limit the scope of the invention. Other aspects, advantages and modifications within the scope of the invention will be apparent to those skilled in the art to which the invention pertains.

All patents, patent applications, journal articles, and other references cited herein are incorporated by reference in their entireties.

Example 1

Preparation of Flavored Lozenges

Lozenges were prepared by mixing 0.4 g ETHOCEL® Standard 45 Premium (obtained from The Dow Chemical Company, Midland, Mich.), 0.38 g peppermint oil, and 0.16 g sucralose at room temperature and ambient humidity. Admixture of the components resulted in a soft, wet composition that was allowed to set for 24 hours in the form of a sheet, and lozenges were then cut therefrom. The lozenges were soft, pliable, and nontacky, and provided sustained release of the peppermint flavor for approximately 4 hours.

Example 2

Preparation of Zinc Acetate Lozenges

Lozenges were prepared by mixing 0.40 g ETHOCEL® Standard 45 Premium, 0.38 g peppermint oil, 0.075 g zinc acetate, and 0.16 g sucralose at room temperature and ambient humidity. Admixture of the components resulted in a soft, wet composition that was formed into a cylinder and allowed to set for 24 hours. Then, 5 lozenges each weighing 0.2 g were cut. Using the alkaline Zincon reagent to assay for zinc, release curves were generated when zinc lozenges were placed in 100 ml of water at room temperature. At 24 hours, about 21% of the zinc was released. In the oral environment of a human test subject, after 1 hour in the mouth, the lozenge was tested for remaining zinc and it was found that 40% of the zinc had been released with 60% still remaining in the lozenge.

Example 3

Preparation of Zinc Chloride Lozenges

Lozenges were prepared by mixing 0.40 g ETHOCEL® Standard 45 Premium, 0.38 g peppermint oil, 0.075 g zinc chloride, and 0.16 g sucralose at room temperature and ambient humidity. Admixture of the components resulted in a soft, wet composition that was formed into a cylinder and allowed to set for 24 hours. Then, 5 lozenges each weighing 0.2 g were cut. Using the alkaline Zincon reagent to assay for zinc, release curves were generated when zinc lozenges were placed in 100 ml of water at room temperature. At 24 hours, about 37% of the zinc was released.

Example 4

Preparation of Zinc Citrate Lozenges

Lozenges were prepared by mixing 0.40 g ETHOCEL® Standard 45 Premium, 0.38 g peppermint oil, 0.075 g zinc citrate, and 0.16 g sucralose at room temperature and ambient humidity. Admixture of the components resulted in a soft, wet composition that was formed into a cylinder and allowed to set for 24 hours. Then, 5 lozenges each weighing 0.2 g were cut. Using the alkaline Zincon reagent to assay for zinc, release curves were generated when zinc lozenges were placed in 100 ml of water at room temperature. At 24 hours, about 3% of the zinc was released. In the oral environment of a human test subject, after 1 hour in the mouth, the lozenge was tested for remaining zinc and it was found that 10% of the zinc had been released with 90% still remaining in the lozenge.

Example 5

Preparation of Zinc Gluconate Lozenges

| Component | Weight (g) | wt. % |
| --- | --- | --- |
| ETHOCEL | 0.4 | 34.0 |
| Peppermint oil | 0.416 | 35.4 |
| Sucralose | 0.16 | 13.6 |
| Zinc gluconate | 0.2 | 17.0 |
| Total weight | 1.176 | |

Lozenges were prepared according to the above table by mixing 0.40 g ETHOCEL® Standard 45 Premium, 0.416 g peppermint oil, 0.2 g zinc gluconate, and 0.16 g sucralose at room temperature and ambient humidity. Admixture of the components resulted in a soft, wet composition that was formed into a cylinder and allowed to set for 24 hours. Then, 2 lozenges each weighing 0.57 g were cut. Using the alkaline Zincon reagent to assay for zinc, release curves were generated when zinc lozenges were placed in 100 ml of water at room temperature. At 10.5 hours, about 83% of the zinc was released. In the oral environment of a human test subject, after 1 hour in the mouth, the lozenge was tested for remaining zinc and it was found that 32% of the zinc had been released with 70% still remaining in the lozenge.

Example 6

Preparation of Zinc Gluconate Lozenges

| Component | Weight (g) | wt. % |
| --- | --- | --- |
| ETHOCEL | 0.4 | 29.1 |
| Peppermint oil | 0.416 | 30.2 |
| Sucralose | 0.16 | 11.6 |
| Zinc gluconate | 0.4 | 29.1 |
| Total weight | 1.376 | |

The procedure of Example 5 was repeated to provide the zinc gluconate lozenge as indicated in the above table. As may be seen, the total weight of zinc gluconate in this lozenge was twice that of the lozenge of Example 5, and the wt. percent here is 29.1, as opposed to 17.0 in the preceding example. Here, the total amount of zinc released at any given time point was greater than that observed with the lozenge of Example 5, and the overall release rate was somewhat increased.

Example 7

Preparation of Vitamin C/Zinc Gluconate Lozenges

| Component | Weight (g) | wt. % |
| --- | --- | --- |
| ETHOCEL | 0.4 | 28.8 |
| Orange oil | 0.51 | 36.7 |
| Sucralose | 0.16 | 11.5 |
| Zinc gluconate | 0.2 | 14.4 |
| Vitamin C | 0.12 | 8.6 |
| Total weight | 1.39 | |

The procedure of Example 5 was repeated to provide the vitamin C/zinc gluconate lozenge as indicated in the above table. As may be seen, the combined weight of the active agents (vitamin C and zinc gluconate) was 0.32 g, representing 23 wt. % of the lozenge. Here, the total amount of zinc and vitamin C released at each time point was greater than that observed with the lozenge of Example 5, and the overall release rate was approximately somewhat less than that observed with the lozenge of Example 6.

Example 8

Preparation of Vitamin C Lozenges

Since vitamin C is water soluble and is continuously eliminated in the urine after ingestion, a long-lasting lozenge releasing vitamin C over a period of at least an hour is desirable. The vitamin C lozenges were prepared by mixing 0.40 g ETHOCEL® Standard 45 Premium, 0.45 g lime oil, 0.30 g ascorbic acid, and 0.10 g sucralose at room temperature and ambient humidity. Admixture of the components resulted in a soft, wet composition that was formed into a cylinder and allowed to set for 24 hours. Then, 5 lozenges each weighing 0.2 g were cut. In the oral environment of a human test subject, the lozenges released flavor and thus the vitamin C for over a two-hour period.

Example 9

Preparation of Sore Throat Lozenges

Lozenges were prepared by mixing 0.40 g ETHOCEL® Standard 45 Premium, 0.38 g peppermint oil, 0.10 g menthol, and 0.20 g sucralose at room temperature and ambient humidity. Admixture of the components resulted in a soft, wet composition that was formed into a cylinder and allowed to set for 24 hours. Then, 5 lozenges each weighing 0.2 g were cut. In the oral environment of a human test subject, the lozenges lasted two hours, with good peppermint and menthol taste throughout the time period, with the menthol producing an anesthetic effect.

Example 10

Preparation of Sore Throat Lozenges

Lozenges were prepared according to the method of Example 8, except that the level of menthol was increased to 0.2 g. The anesthetizing effect was found to be stronger with the increased quantity of menthol.

Example 11

Preparation of Sore Throat Lozenges

Lozenges were prepared by mixing 0.40 g ETHOCEL® Standard 45 Premium, 0.38 g peppermint oil, 0.10 g benzocaine, and 0.16 g sucralose at room temperature and ambient humidity. Admixture of the components resulted in a soft, wet composition that was formed into a cylinder and allowed to set for 24 hours. Then, 5 lozenges each weighing 0.2 g were cut. In the oral environment of a human test subject, the numbing effect of the benzocaine was experienced for over two hours.

Example 12

Evaluation of Factors Affecting Release Rates

In order to determine the effect of various formulation parameters on release profile from dosage forms of the invention, the following lozenge formulations were prepared with methylene blue used as the beneficial agent.
Formulation 1: Standard Formulation, Used as Control
 0.4 g Ethocel 45
 0.16 g Sucralose
 50 mg Methylene Blue
 26 drops peppermint oil (0.42 g)
Formulation 2: 25% Additional Ethocel 7
 0.4 g ETHOCEL® Standard 45 Premium
 0.1 g Ethocel 7
 0.16 g Sucralose
 50 mg Methylene Blue
 33 drops peppermint oil (0.53 g)
Formulation 3: 100% Increased Sucralose
 0.4 g ETHOCEL® Standard 45 Premium
 0.32 g Sucralose
 50 mg Methylene Blue
 33 drops peppermint oil (0.53 g)
Formulation 4: Increased Ethocel 45
 0.5 g ETHOCEL® Standard 45 Premium
 0.16 g Sucralose
 50 mg Methylene Blue
 33 drops peppermint oil (0.53 g)
Formulation 5: Ethocel 7 (Instead of Ethocel 45)
 0.4 g Ethocel 7
 0.16 g Sucralose
 50 mg Methylene Blue
 26 drops peppermint oil (0.42 g)
Formulation 6: 1.5 Times More Peppermint Oil
 0.4 g ETHOCEL® Standard 45 Premium
 0.16 g Sucralose
 50 mg Methylene Blue
 40 drops peppermint oil (0.64 g)

The lozenges were placed in 100 ml of water and the absorbance at 668 nm was monitored to determine the release of methylene blue at various times. The results are summarized in the following table.

Release Rates: % Methylene Blue Released

| Time (hr) | Formulation 1* | Formulation 2 | Formulation 3 | Formulation 4 | Formulation 5 | Formulation 6 |
|---|---|---|---|---|---|---|
| 0.5 | 4.5 | 4.2 | 7.1 | 5.4 | 2.6 | 2.4 |
| 1 | 6 | 5.1 | 8.9 | 7 | 3.3 | 3.3 |
| 2 | 7.5 | 6.3 | 11.9 | 9.4 | 4.3 | 4.1 |
| 9.5 | 12 | 7.7 | 18 | 11.8 | 4.9 | 4.6 |
| 16 | 15 | 8.5 | 20.4 | 13.3 | 5.4 | 4.8 |
| 24 | 18 | 8.7 | 23.5 | 14.8 | 6.6 | 5.5 |

*Average of 2 runs

As may be deduced from the table, addition of the low molecular weight hydrophilic polymer (Ethocel 7; Formulation 2) and substitution of the lower molecular weight hydrophilic polymer for the moderate molecular weight polymer (Formulation 5) decrease release rate somewhat, as does an increase in the proportion of the essential oil (Formulation 6). Incorporation of additional moderate molecular weight hydrophilic polymer (Formulation 4) also decreased the release rate, but not as significantly. By contrast, increasing the relative amount of sucralose (Formulation 3) provided a noticeable increase in release rate.

Example 13

Additional Release Rate Studies (Zinc Gluconate)

Zinc gluconate formulations were prepared to evaluate the effect of the amount of zinc in the dosage form on the rate at which zinc is released therefrom. The two formulations were as follows: Formulation 7-0.2 g zinc gluconate, 0.4 g Ethocel 45, 0.16 g sucralose, 0.5 ml peppermint oil; Formulation 8-0.4 g zinc gluconate, 0.4 g Ethocel 45, 0.16 g sucralose, 0.5 ml peppermint.

| Time (hr) | % Release of Zn from Formulation 7 | % Release of Zn from Formulation 8 |
|---|---|---|
| 0.5 | 11 | 14 |
| 1 | 14 | 19 |
| 2 | 17 | 31 |
| 10 | 83 | 100 |

When administered in vivo, the percent of zinc released after 1 hour in the mouth was about 25-40%.

Example 14

Additional Release Rate Studies (Flavored Lozenge)

A lozenge was prepared as described in Example 1 containing 0.1 g of Ethocel 7 and 5 drops of peppermint oil. The amount of peppermint released over time was as follows:

| Time (hr) | % Release |
|---|---|
| 0.5 | 9.7 |
| 1 | 13.4 |
| 2 | 20.7 |
| 3 | 26 |
| 4 | 34 |
| 15 | 64 |
| 24 | 81 |

In vivo, the lozenges released most of the peppermint within about 3-4 hours and then broke apart.

Example 15

Additional Studies on Factors Controlling Release and Disintegration Rates (a) In order to further clarify the effect of molecular weight on release kinetics and lozenge disintegration, the following formulations were prepared:
Formulation 9
 0.4 g ETHOCEL® Standard 100 Premium 0.2 g sucralose
 0.2 g gum acacia
 0.05 g stearic acid
 0.12 g citric acid
 0.076 g glycerol
 0.41 g lemon oil Formulation 10
    0.4 g ETHOCEL® Standard 10 Premium
    0.2 g sucralose 0.2 g gum acacia 0.05 g stearic acid
    0.12 g citric acid
    0.076 g glycerol
    0.41 g lemon oil The formulations were made by admixing all components at room temperature and ambient humidity, and then pressing the mixture into lozenges of about 0.42 g each. Lozenges prepared from Formulation 9, containing the high molecular weight ethylcellulose, disintegrated and released flavors and other components within 3 minutes, while the corresponding lozenges of Formulation 10, containing the low molecular weight ethylcellulose, disintegrated and released flavors and other components over a 30 minute time period. Accordingly, use of the high viscosity ethylcellulose gives rise to a lozenge with more rapid release kinetics and disintegrates more quickly, given an equivalent amount of essential oil in the polymer matrix.

(b) Two further formulations were prepared and lozenges made therefrom using the aforementioned mix-and-compaction method, in which both molecular weight and the amount of essential oil were varied:

Formulation 11
    0.4 g ETHOCEL® Standard 45 Premium
    0.2 g sucralose
    26 drops peppermint oil (0.42 g)

Formulation 12
    0.4 g ETHOCEL® Standard 7 Premium
    0.2 g sucralose
    13 drops peppermint oil (0.21 g)

Both lozenges lasted about 3 hours, although the flavor intensity of Formulation 12 was lower than in Formulation 11. It may be concluded that polymer matrices of similar strength may be prepared using far less of the flavoring agent provided that a lower molecular weight polymer is also employed.

(c) Preparation of extra long-lasting gums and lozenges: The effect of the amount of essential oil present on release rate and disintegration was then evaluated by comparing two gum formulations that were identical except for the amount of essential oil present:

Formulation 13
    0.4 g ETHOCEL® Standard 45 Premium
    0.3 g sucralose
    0.45 g peppermint oil
    5 g gum base
    glycerol (as needed to facilitate mixing)

Formulation 14
    0.4 g ETHOCEL® Standard 45 Premium
    0.3 g sucralose
    0.58 g peppermint oil
    5 g gum base
    glycerol (as needed to facilitate mixing)

The gum formulations prepared by mixing the Ethocel, sucralose, and peppermint oil, adding the mixture to the gum base that had been softened by heating at 120° C., and adding minute amounts of glycerol to aid in the mixing process. The gum was formed by pressing. The gum prepared from Formulation 13, containing a lower amount of the essential oil, provided flavor that lasted about 40 minutes, while the gum prepared from Formulation 14, containing a higher level of the essential oil, provided flavor over a period of approximately 1.5 hours.

Lozenges containing methylene blue were then prepared with different ratios of essential oil to polymer, from Formulations 15 and 16:

Formulation 15
    0.4 g ETHOCEL® Standard 45 Premium
    0.16 g sucralose
    0.42 g peppermint oil
    0.05 g methylene blue Formulation 16
    0.64 g ETHOCEL® Standard 45 Premium
    0.16 g sucralose
    0.42 g peppermint oil
    0.05 g methylene blue The lozenges were prepared using the mix-and-compaction method above, and placed in 100 ml water for 24 hours. The lozenges prepared from Formulation 15, having a higher essential oil to polymer ratio, released approximately 18% of the original amount of methylene blue after 24 hours, while the lozenges prepared from Formulation 16, having a lower essential oil to polymer ratio, released only 5.5% of the methylene blue after 24 hours. As with the gums, then, the lozenges having a higher essential oil to polymer ratio exhibited a faster release rate.

Example 16

Preparation of Gradually Eroding Lozenges

Lozenges of about 0.4 g each were prepared using the mix-and-compaction method of Example 15, using 0.40 g ETHOCEL® Standard 45 Premium, 0.42 g peppermint oil, 0.2 g calcium polycarbophil, and 0.42 g sucralose. Addition of the carbophil to the formulation improved cohesiveness and resulted in gradual erosion of the lozenge over a 2.5 hour time period, without disintegration into relatively large lozenge pieces.

Example 17

Preparation of Gradually Eroding Zinc Gluconate Lozenges

Zinc gluconate lozenges of about 0.4 g each were prepared using the mix-and-compaction method of Example 15, using 0.40 g ETHOCEL® Standard 45 Premium, 0.46 g peppermint oil, 0.2 g calcium polycarbophil, 0.4 zinc gluconate, and 0.32 g sucralose. As with the lozenges prepared and evaluated in the preceding example, gradual erosion was observed without disintegration into sizable fragments.

Example 18

Preparation of Gradually Eroding Lozenges

Lozenges of about 0.4 g each were prepared using the mix-and-compaction method of Example 15, using 0.40 g ETHOCEL® Standard 45 Premium, 0.46 g peppermint oil, 0.2 g calcium polycarbophil, 0.025 g Polyox® WSR N-10, and 0.32 g sucralose. With the addition of the polyethylene oxide to the formulation, gradual erosion of the lozenge in the mouth felt very much like the lozenge was actually dissolving.

Example 19

Lozenges with Shorter Release Rates and Disintegration Times

The following formulations were used to prepare lozenges that were then evaluated to determine the effect of a disintegrants on release rate and disintegration time:

Formulation 17
  0.23 g glycerol
  0.29 g peppermint oil
  0.4 ETHOCEL® Standard 45 Premium
  0.3 g sucralose
  0.2 g gum acacia
  0.05 g stearic acid
Formulation 18
  0.38 g glycerol 0.29 g peppermint oil
  0.4 ETHOCEL® Standard 45 Premium 0.3 g sucralose 0.2 g gum acacia 0.05 g stearic acid The lozenges were prepared by first mixing the glycerol and peppermint oil, and then adding that mixture to a powder blend of the polymer, sucralose, gum acacia, and stearic acid. The lozenges prepared weighed about 0.44 g. The lozenge prepared from Formulation 17 disintegrated within 30 minutes, while the lozenge containing a higher level of glycerol, prepared from Formulation 18, disintegrated within only 3 minutes.

Example 20

Diphenhydramine Lozenges

Diphenhydramine lozenges were prepared by mixing 0.40 g ETHOCEL® Standard 45 Premium, 0.05 g diphenhydramine, and 0.47 g lemon oil, then adding 0.12 g glycerol and mixing again, and finally adding a powder mixture of 0.2 g gum acacia, 0.1 g sucralose, 0.05 g stearic acid, and 0.7 g Confectioner's sugar (corn starch). Lozenges of about 0.4 g were prepared using the mix-and-compaction method of Example 15. The bitter taste of the active agent was effectively masked, and release and disintegration occurred within about 5 minutes.

Example 21

ASA Lozenges

Acetylsalicylic acid (ASA; aspirin)-containing lozenges were prepared by the mix-and-compaction method of Example 15 from 0.40 g ETHOCEL® Standard 45 Premium, 1.0 g ASA, 0.6 g sucralose, 0.2 g polycarbophil, 0.1 g Polyox® WSR N-10, and 0.48 g peppermint oil. The lozenges, about 0.45 each, provided for release over an approximately 40-minute period, at which point the lozenges disintegrated.

Example 22

Dexamethasone Lozenges

Dexamethasone lozenges of about 0.4 g each were prepared by the mix-and-compaction method of Example 15 from 0.80 g ETHOCEL® Standard 45 Premium, 0.64 g sucralose, 10 mg dexamethasone (dissolved in 12 drops of ethanol to which 50 drops of orange oil were added), 0.4 g benzocaine, 0.4 g sorbitol, and 0.2 g polycarbophil. The resulting lozenges are useful in the treatment of oral sores, including cold sores and oral mucositis, with patients reporting that sores that had previously taken about 2 weeks to heal were completely healed using the aforementioned lozenges as needed.

Example 23

Evaluation of MSM as a Permeation Enhancer

In order to evaluate the utility of methyl sulfonyl methane (MSM) as a permeation enhancer, the following experiment was carried out. A 27 mg/ml aqueous solution of MSM was added to 1 mg/ml of methylene blue in a vial sealed with porcine intestinal membrane, and the diffusion of the methylene blue through the membrane and into the water was observed. For the comparison, the same procedure was carried out with an equivalent volume of a 270 mg/ml aqueous solution of MSM. The results indicated that the lower concentration admixture resulted in a rate of penetration 1.3 times higher than the control (1 mg/ml methylene blue; no MSM), while the higher concentration admixture resulted in a rate of penetration 2.0 times higher than the control.

Example 24

Taste-Masked Formulations

ETHOCEL® Standard 7, 45, and 100 (Premium) were compared in an experiment designed to evaluate the effectiveness of the present matrices in providing taste masking of a bitter drug, diphenhydramine. The matrices were formed by mixing 0.1 g ETHOCEL®, 0.05 g diphenhydramine, and 0.24 g peppermint oil to form a translucent slurry. Xylitol, 2.25 g, was added to the matrix and the matrix was further mixed to form a xylitol-coated granulated matrix. The masking of the drug's taste was good in all cases, although the efficacy of taste masking increased with the molecular weight of the polymer.

We claim:

1. A flavored dosage form comprising a lozenge, wherein the lozenge comprises a sustained release matrix of:
   (a) micronized ethylcellulose having a solution viscosity in the range of approximately 1 cP to 120 cP as determined at 25° C. using a 5% aqueous solution and representing approximately 25 wt. % to 49.5 wt. % of the lozenge; and
   (b) a flavoring agent comprising mint oil essential oils, and optionally, constituents of mint oil essential oils, the mint oil essential oils representing approximately 25 wt. % to 49.5 wt. % of the lozenge,
   wherein the micronized ethylcellulose and the flavoring agent are admixed and present in the dosage form at a weight ratio of approximately 1:1.5 to 1.5:1, such that the dosage form has a soft, pliable consistency and gradually erodes in the mouth while simultaneously gradually releasing the flavoring agent over an extended time period in the range of about 15 minutes to about 4 hours, and
   wherein the sustained release matrix is formed by a process consisting essentially of admixing the micronized ethylcellulose and the essential oil flavoring agent at room temperature and ambient humidity.

2. The dosage form of claim 1, wherein the extended time period is in the range of about 15 minutes to about 60 minutes.

3. The dosage form of claim 1, wherein the extended time period is at least 60 minutes.

4. The dosage form of claim 3, wherein the extended time period is at least 2 hours.

5. The dosage form of claim 1, wherein the micronized ethylcellulose has a solution viscosity in the range of approximately 3 to 100 cP.

6. The dosage form of claim 5, wherein the solution viscosity is in the range of approximately 6 to 49 cP.

7. The dosage form of claim 1, wherein the mint oil is selected from peppermint oil, spearmint oil, or a combination thereof.

8. The dosage form of claim 1, further including an effective sweetening amount of a sweetener.

9. The dosage form of claim 8, wherein the sweetener comprises a sweetening agent selected from aspartame, saccharin, sodium saccharin, calcium saccharin, sucralose, acesulfame-K, sorbitol, xylitol, steviosin, steviol, mannitol, erythritol, lactitol, or mixtures thereof.

10. The dosage form of claim 1, further comprising a colorant.

11. The dosage form of claim 1, further including at least one additive selected from release rate accelerants, release rate retardants, adhesion-increasing agents, adhesion-reducing agents, flavor stabilizers, flavor diluents, pH-adjusting agents, preservatives, lubricants, and fillers.

12. The dosage form of claim 9, wherein the sweetener comprises xylitol.

13. The dosage form of claim 1, wherein the micronized ethylcellulose has an ethoxyl content in the range of about 45.0% to 52.0%.

14. The dosage form of claim 1, wherein the micronized ethylcellulose has a mean particle size of about 20 microns.

15. The dosage form of claim 1, wherein the micronized ethylcellulose has a solution viscosity in the range of approximately 90 to 110 cP.

16. The dosage form of claim 14, wherein the micronized ethylcellulose has a solution viscosity in the range of approximately 90 to 110 cP.

17. The dosage form of claim 11, wherein the at least one additive is present in the range of about 1 wt. % to 45 wt. % of the lozenge.

18. The dosage form according to claim 1, wherein the sustained release matrix is formed by a process further comprising:
 allowing the admixture of the micronized ethylcellulose and the essential oil flavoring agent to set and cutting the matrix to provide the lozenge.

* * * * *